US00PP11007P

United States Patent [19]

Zary

[11] Patent Number: Plant 11,007

[45] Date of Patent: Jul. 13, 1999

[54] HYBRID TEA ROSE PLANT NAMED 'JACPIHI'

[75] Inventor: Keith W. Zary, Thousand Oaks, Calif.

[73] Assignee: Bear Creek Gardens, Inc., Medford, Oreg.

[21] Appl. No.: 09/024,253

[22] Filed: Feb. 17, 1998

Related U.S. Application Data

[51] Int. Cl.[6] ..... A01H 5/00

[52] U.S. Cl. ..... Plt./133

[58] Field of Search ..... Plt./124, 133, 134

*Primary Examiner*—Howard J. Locker

*Attorney, Agent, or Firm*—Klarquist Sparkman Campbell Leigh & Whinston, LLP

[57] ABSTRACT

Hybrid tea rose plant having attractive, well formed white flowers; long, straight stems; vigorous, upright, well branched growth habit; and large, dark green, rust resistant foliage.

1 Drawing Sheet

The present invention relates to a new and distinct variety of rose plant of the hybrid tea class which was originated by me by crossing 'JAColite' (U.S. Plant Pat. No. 4167), with 'JACpico' (U.S. Plant Pat. No. 3997).

The primary objective of this breeding was to produce a new rose variety having the long stems, vigorous growth and white flower color of the female parent, combined with the excellent flower form, good vigor and large, disease resistant foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Attractive, well formed white flowers;
2. Long, strong stems;
3. Vigorous, upright, well branched growth habit;
4. Large, dark green, rust resistant foliage.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JAColite' (U.S. Plant Pat. No. 4,167).

*Pollen parent.*—'JACpico' (U.S. Plant Pat. No. 3,997).

Classification:

*Botanical.*—Rosa hybrida.

*Commercial.*—Hybrid tea.

FLOWER

Observations made from specimens grown in a garden environment at Somis, Calif. from January to October, 1997.

Blooming habit: Recurrent.

Bud:

*Size.*—1¾" long when the petals start to unfurl.

*Form.*—The bud form is long, pointed ovoid.

*Color.*—When sepals first divide, bud color is Yellow White Group 158B. When half blown, the upper sides of the petals are White Group 155B and the lower sides of the petals are White Group 155B.

*Sepals.*—Color: Green Group 138B, sometimes quite bronzy in bright sun. Surface texture: Covered in fine hairs. There are three normally to heavily appendaged sepals. There are two unappendaged sepals with hairy edges.

*Receptacle.*—Color: Yellow Green Group 146B. Shape: Funnel. Size: Medium (5/16"×¼"). Surface: Smooth.

*Peduncle.*—Length: Short (2½"). Surface: Very glandular. Color: Medium green. Strength: Stiff, erect.

Bloom:

*Size.*—Large. Average open size is 4".

*Borne.*—Singly.

*Stems.*—Long (18–22"), strong.

*Form.*—When first open: High centered. Permanence: Retains its form to the end, outer petals curl back.

*Petalage.*—Number of petals under normal conditions: 30.

*Color.*—The upper sides of the petals are White Group 155B. The reverse sides of the petals are White Group 155B. The base of each petal has a small, (3/16"×3/16"), Yellow Group 4C half moon at the point of attachment. The major color on the upper sides is White Group 155B.

*Variegations.*—Occasional greenish white streak on the guard petals.

*Discoloration.*—No change through day six or seven when petals fall.

*Fragrance.*—Moderate.

Petals:

*Texture.*—Thick.

*Shape.*—Round.

*Form.*—Tips slightly recurved, edges slightly quilled.

*Arrangement.*—Imbricated. Petaloids in the center are few.

*Persistence.*—Petals drop off cleanly before drying.

*Lastingness.*—On the plant: Long (6–7 days). As a cut flower: Long (9–10 days).

Reproductive parts:

*Anthers.*—Size: Medium. Quantity: Many. Color: Yellow. Arrangement: Regular around styles.

*Filaments.*—Color: Yellow.

*Pollen.*—*Color: Lemon yellow.*

*Styles*.—Color: Red.
*Stigmas*.—Color: Greenish white.

Plant:
*Form*.—Bush.
*Growth*.—Vigorous; upright; branching: Height of mature plant is five to five and one half feet, width is four feet.

Foliage:
*Number of leaflets on normal mid-stem leaves*.—Five or seven.
*Size*.—Large (6 to 6½"×5").
*Quantity*.—Abundant.
*Color*.—*New foliage: Upper and lower sides: Greyed Orange Group* 176A. Old foliage: Upper side: Green Group 139A. Lower side: Green Group 138C.

Leaflets:
*Shape*.—Broadly oval.
*Texture*.—Upper side: Leathery.
*Edge*.—Serrated.
*Serration*.—Single, small.
*Petiole rachis*.—Color: Green.
*Petiole underside*.—Smooth, with occasional prickles.
*Stipules*.—Medium, (½"), serrated, bearded.
*Disease resistance*.—*Susceptible to mildew, but resistant to rust under normal growing conditions at Somis, Calif.*

Wood:
*New wood*.—Color: Reddish. Bark: Smooth.
*Old wood*.—Color: Green. Bark: Smooth.

Prickles:
*Quantity*.—*On main canes from base: Ordinary. On laterals from main canes: Ordinary.*
*Form*.—Medium, hooked downward.
*Color when young*.—Red.

Small prickles:
*Quantity*.—On main stalks: Few to none. On laterals: Few to none.

I claim:

1. A new and distinct variety of rose plant of the hybrid tea class, substantially as herein shown and described, characterized particularly as to novelty by the unique combination of its attractive, well formed white flowers; long, straight stems; vigorous, upright, well branched growth habit; and large, dark green, rust resistant foliage.

* * * * *

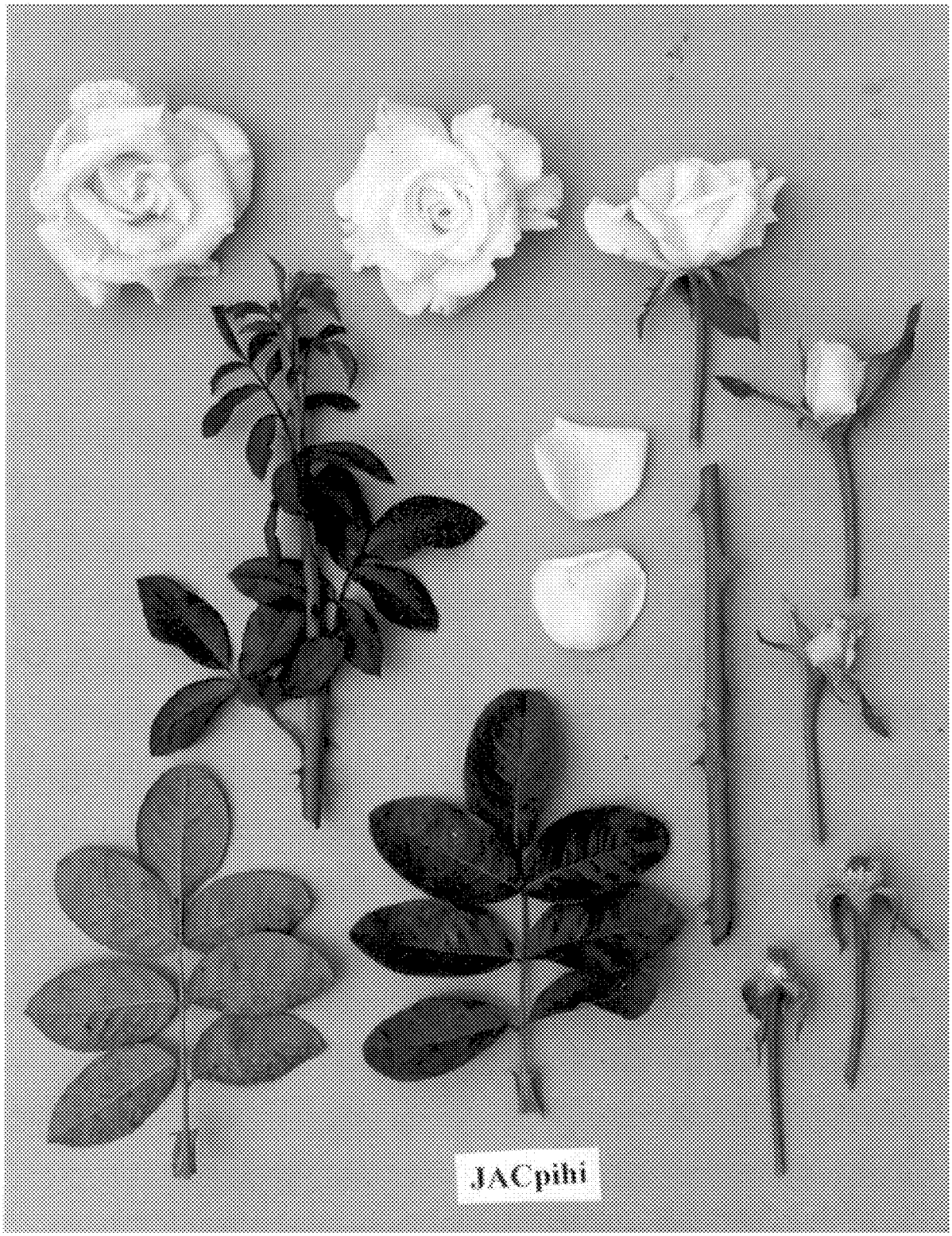
JACpihi